United States Patent
Kil et al.

(10) Patent No.: US 8,655,675 B2
(45) Date of Patent: Feb. 18, 2014

(54) SYSTEM AND METHOD FOR PROVIDING INDIVIDUALLY TAILORED HEALTH-PROMOTING INFORMATION

(75) Inventors: David H. Kil, Prospect, KY (US); Bongjoo Shin, Prospect, KY (US)

(73) Assignee: Humana Inc., Louisville, KY (US)

( * ) Notice: Subject to any disclaimer, the term of this patent is extended or adjusted under 35 U.S.C. 154(b) by 1664 days.

(21) Appl. No.: 11/478,888

(22) Filed: Jun. 30, 2006

(65) Prior Publication Data

US 2007/0179351 A1    Aug. 2, 2007

Related U.S. Application Data

(60) Provisional application No. 60/695,359, filed on Jun. 30, 2005.

(51) Int. Cl.
    G06F 19/00 (2011.01)
    G06Q 10/00 (2012.01)
    G06Q 50/00 (2012.01)
    A61B 5/00 (2006.01)

(52) U.S. Cl.
    USPC .................................. 705/2; 705/3

(58) Field of Classification Search
    USPC ....................................... 705/2–3
    See application file for complete search history.

(56) References Cited

U.S. PATENT DOCUMENTS

| | | | | |
|---|---|---|---|---|
| 5,676,551 | A * | 10/1997 | Knight et al. | 434/236 |
| 5,692,501 | A * | 12/1997 | Minturn | 600/301 |
| 5,961,332 | A * | 10/1999 | Joao | 434/236 |
| 6,470,352 | B2 * | 10/2002 | Yaginuma | 1/1 |
| 2003/0004788 | A1 * | 1/2003 | Edmundson et al. | 705/10 |
| 2003/0177037 | A1 * | 9/2003 | Oka et al. | 705/2 |
| 2003/0229284 | A1 * | 12/2003 | Stein | 600/454 |
| 2004/0122715 | A1 * | 6/2004 | McAuliffe | 705/2 |
| 2004/0243443 | A1 * | 12/2004 | Asano et al. | 705/2 |
| 2005/0015276 | A1 * | 1/2005 | Sullivan et al. | 705/2 |
| 2006/0161461 | A1 * | 7/2006 | Trani et al. | 705/4 |
| 2007/0272011 | A1 * | 11/2007 | Chapa et al. | 73/379.01 |

OTHER PUBLICATIONS

Penhollow et al., "Sexual Desrability and Sexual Performance: Does Exercise and Fitness Really Matter?", Oct. 2004, Electronic Journal of Human Sexuality, vol. 7, p. 1-4.*
Merriam-Webster Online Dictionary, 2010, Merriam-Webster Online, Retrieved Jun. 3, 2010, www.merriam-webster.com/dictionary/psychosocial.*
Merriam-Webster Online Dictionary, 2010, Merriam-Webster Online, Retrieved Jun. 3, 2010, www.merriam-webster.com/dictionary/hierarchy.*
Penhollow et al., "Sexual Desirability and Sexual Performance: Does Exercise and Fitness Really Matter?", Oct. 2004, Electronic Journal of Human Sexuality, vol. 7, p. 1-4.*
International Search Report, Form PCT/ISA/210, 2 pages, for International Application No. PCT/US06/25606 completed on Jun. 18, 2008 and mailed Aug. 1, 2008.

* cited by examiner

*Primary Examiner* — Joy Ching
(74) *Attorney, Agent, or Firm* — Bingham Greenebaum Doll LLP; James C. Eaves, Jr.; Brian W. Chellgren (57) ABSTRACT

A system and method for providing to an individual certain information which is relevant to that individual's health status. More specifically, the invention relates to a system and method for providing information relevant to an individual's health status and wherein the information provided is chosen on the basis of not only the individual's health status but also complex psychosocial behavioral factors related to that individual's motivational structure and likely impact.

12 Claims, 2 Drawing Sheets

SYSTEM AND METHOD FOR PROVIDING INDIVIDUALLY TAILORED HEALTH-PROMOTING INFORMATION

This application claims the benefit of U.S. provisional patent application, Ser. No. 60/695,359, filed Jun. 30, 2005, for a system and method for providing individually tailored health-promoting information, incorporated herein by reference.

BACKGROUND OF THE INVENTION (a) Field of the Invention

The present invention relates to a system and method for providing to an individual certain information which is relevant to that individual's health status. More specifically, the invention relates to a system and method for providing information relevant to an individual's health status and wherein the information provided is chosen on the basis of not only the individual's health status but also complex psychosocial behavioral factors related to that individual's motivational structure and likely impact.

It has long been a goal of healthcare providers and health services researchers to provide information to an individual that does not merely confer a momentary cognitive benefit to the individual but also motivates that individual to act to improve his or her health. This goal has proven difficult to attain, especially when it is proposed to provide such information to a large population of individuals, each of whom is in need of healthcare information that is tailored to address his or her health status in the context of the real-life psychosocial situation in which the individual is found. The present invention accomplishes that goal, through providing a method and a system for providing individually tailored health-related information to an individual in a way that facilitates that individual's acting on the basis of that information to improve his or her health.

(b) Description of the Prior Art

Studies summarized and analyzed by Victor J. Strecher and Matthew W. Kreuter have shown that motivational factors are not taken adequately into account when individuals are confronted en masse with health assessments and attendant recommendations, when those recommendations are generic rather than individually tailored. The individuals typically gain some potentially useful information from such assessments and recommendations, but many individuals in greatest need of lifestyle change or facilitation of healthier choice-making are those who respond most ineffectively, or not at all, to the provision of such information. Strecher and Kreuter recommended that feedback be provided having the following characteristics: "allows the user to understand his or her risk status relative to others in the population . . . allows the user to better understand the relative risks of diseases he or she is at risk of suffering . . . allows the user to better understand the relative impact of various risk factors . . . allows the user to understand the health benefits of specific behavioral changes . . . enhances the user's ability to make recommended health behavior changes."

SUMMARY OF THE INVENTION

The present invention relates to a system and method for providing to an individual certain information which is relevant to that individual's health status. More specifically, the invention relates to a system and method for providing information relevant to an individual's health status and wherein the information provided is chosen on the basis of not only the individual's health status but also complex psychosocial behavioral factors related to that individual's motivational structure and likely impact.

More particularly, the system for providing individually tailored health-promoting information of the present invention comprises: a server system including a response database containing individual responses to health risk assessment questions, behavior questions, lifestyle questions, and family history questions, a claims database, and a processor; the server system creating a multidimensional map position for an individual from information on the individual contained in the response database and the claims database. The server system can further include a content database, the server system providing appropriately tailored content for the individual from the content database based on the individual's multidimensional map position.

The system can further comprise at least one user computer which provides the individual access to the server system to receive that individual's appropriately tailored content. Also, this at least one user computer can permit the individual to provide information for the response database related to that individual. The individual's appropriately tailored content can include recommendations and motivational messages tailored to that individual's psychosocial behavioral characteristics.

The individual's multidimensional map position can be based on available information on that individual contained in the response database and the claims database concerning that individual's clinical and disease history and that individual's behavioral and lifestyle and family history. The individual's appropriately tailored content can be based on available information on that individual contained in the response database and the claims database concerning that individual's weight, eating habits, exercise habits, family support structure, stress management, hobbies/activities, smoking/non-smoking, sleep habits, disease conditions, emotional issues, age, and gender. The individual's appropriately tailored content can be further based on available information on that individual contained in the response database and the claims database concerning that individual's self-efficacy, motivation, value hierarchy, and faith.

The present invention also is for a method for providing individually tailored healthy behavior-promoting information to an individual comprising the steps of:
 a. mapping the health status of the individual on the basis of information available concerning the individual with respect to the individual's clinical and disease history and the individual's behavioral and lifestyle and family history, thereby creating a multidimensional map position concerning the individual;
 b. eliciting from the individual one or more answers to questions concerning the individual's preferences and tendencies, thereby creating an answer set concerning the individual; and
 c. providing to the individual, in a format that varies according to the answer set, one or more recommendations concerning one or more behaviors in which the individual can engage in order to maintain or improve the individual's health, In this method, the one or more recommendations provided to the individual can comprise content that varies according to that individual's multidimensional map position and answer set. The one or more recommendations provided to the individual can be based on available information on that individual concerning that individual's weight, eating habits, exercise habits, family support structure, stress management, hobbies/activities, smoking/non-smoking, sleep habits, disease conditions, emotional issues, age, and gender. Also, the one or more recommendations provided to the individual can be further based on available information on that individual concerning that individual's self-efficacy, motivation, value hierarchy, and faith. Even further, the one or more recommendations provided to the individual can include both recommendations and motivational messages tailored to that individual's psychosocial behavioral characteristics.

BRIEF DESCRIPTION OF THE DRAWINGS

A better understanding of the present invention will be had upon reference to the following description in conjunction with the accompanying drawings.

FIG. 1 shows the overall progressive content tailoring logic. Content tailoring and prioritization depend on the embedded hierarchical tree trajectories along the N (needs analysis) and AB (action plan and benefits) directions. The behavior axis in the N trajectory is a discrete set consisting of measures of body mass index or BMI, smoking, drinking/substance abuse, exercise, eating, and information seeking behavior while the emotional-state axis contains measures of loneliness, stress, motivation, self-efficacy, and religiousness or faith. The risk-factor axis in along the AB trajectory for the Q3 population represents the interplay between recommended action plan and how it can reduce risk factors, which can be elucidated in the most appealing way based on the consumer's value hierarchy. The disease-cluster-condition axis follows the chronic conditions consistent with Humana's (Humana Inc. of Louisville, Ky.) disease-management programs and clinical guidance strategy through its Personal Nurse program. One more condition is the premature birth state that will affect the onset of adulthood chronic illnesses. In reality, four quadrants may not be sufficient as in hierarchical wavelet decomposition. In FIG. 1, TIU means tangibles/intangibles/unexpected. PDF means probability density function. $HS_{CH}$ means clinical plus disease history health score and $HS_{BLF}$ means behavioral plus lifestyle plus family history score.

FIG. 2 shows more detailed examples of the progressive content tailoring logic. CF+PSBC+VH+ISB refer to collaborative filtering (hobbies, sports, and fitness+movie/book), psychosocial behavioral clinical profiles (self-efficacy, motivation, MPAA or Motion Pictures Association of America rating for content spice, and # of chronic illnesses), value hierarchy (ranking of power, money, love, faith, family, friends, and health), and information-seeking behavior (Web surfing). In the benefits section, tangible, intangible, and unexpected axes represent quantifiable (economic benefit, improved fitness, improved appearance, etc.), internal (happiness, greater self-confidence), and unexpected (falling in love again). In FIG. 2, SE means socioeconomic. CC means chronic condition.

DETAILED DESCRIPTION OF THE PREFERRED EMBODIMENT

While recommendations such as Strecher's and Kreuter's have been in the literature for some time, still there has not been an appropriately scalable system or method for reliable implementation. It is an object of the invention to accomplish the goal of such recommendations through a system and method for the provision of individually tailored health-promoting information. This is a non-trivial task, as one seeks to gain, through assessment, adequate information about an individual so that useful and practical health-promoting suggestions can be made to him or her while at the same time not burdening that individual with information that has marginal or no relevance to their personal situation, including their psychosocial and attendant motivational structure. What is therefore provided is a system and method for providing information relevant to an individual's health status and wherein the information provided is chosen on the basis of not only the individual's health status but also complex psychosocial factors related to that individual's motivational structure.

The subject system and method accomplish their object through the use of progressive coding. (It should be noted that image compression systems and methods known in the art also make use of progressive coding, for example, embedded zerotree coding.) That is, tailoring is accomplished on multiple levels. In a particularly preferred embodiment, a minimum amount of globally tailored content is provided to a large number of individuals in a manner that is consistent with each of those individuals subsequently engaging in health-promoting behavior suitable for that individual. For example, on a first level, information concerning individual health-related and behavioral information is mapped. On a second level, individual preference- and tendency-related content is tailored to be provided to the individual on the basis of individual behavior-related information. On a third level, individual motivational-structure-related content is tailored to be provided to the individual on the basis of individual motivational-structure-related information.

A first-level tailoring according to the invention may comprise both combinatorial and orthogonal content maps with respect to characteristics of an individual relevant to the individual's health status. A second-level tailoring according to the invention may comprise the provision of content consistent with known preferences or tendencies of the individual. A third-level tailoring according to the invention may comprise the provision of content consistent with aspects of the motivational structure of the individual.

Additional detail for embodiments of the invention is provided below.

Progressive Coding:

The more guidance parameters we have, the sharper and more tailored our feedback becomes. This is conceptually similar to embedded zerotree encoding used in image compression. The biggest benefit is to write the minimum amount of globally tailored content to touch the maximum number of members to help them as best as we can.

1. First-level tailoring: Combinatorial and orthogonal content maps.
  a. Combinatorial (comprehensive).
    i. Clinical+disease history health score ($HS_{CH}$) VS. behavioral+lifestyle+family history $HS_{BLF}$.
    ii. Weight vs. eating vs. exercise→recommendations subject to doctor's order.
    iii. Family support structure (spouse, children, stress at home and work) vs. mental state directly observable or inferred.
  b. Orthogonal (as a branch of the combinatorial parents).
    i. Individual behavioral component (eating, stress, weight, fitness, sleep, smoking).
    ii. Disease conditions: individual and common co-morbid disease clusters.
    iii. Emotional components, especially destructive ones: loneliness, anger, depression, and helplessness.
    iv. Recommended activities.
    v. Prematurely born with or without chronic illness.
    vi. Age, gender, and value hierarchy in benefits.

2. Second-level tailoring: Tailor tailored content.
   a. Behavioral stratification variables, as shown below.
   b. Information-seeking behavior (Web).
   c. Sports or celebrity personalities from the hobby section (Shaq's example of being fat and suffering nagging injuries while he was with the LA Lakers, Tiger, etc.).
      i. Collaborative filtering.
      ii. Add texture and color to recommendation.
   d. Favorite movie/book (what % can we cover using box office ranking and the New York Times (NYT) bestseller list).
   e. Quotation bible—ethnicity, gender, age, and education.
3. Tertiary-level tailoring: Deeper drilldown action plan.
   a. Personal trainer (Kate Lorig's book would be applicable here for example.)
   b. Personal nutritionist (Samsung's Smartcare portal as an example).
   c. Personal nurse.

Behavioral Stratification Variables: Self-efficacy (Low/High); Motivation (L/H); Motion Pictures Association of America (MPAA) rating (G/PG/PG-13/R): for the future; Value hierarchy (power, love, money, family, friends, health, and faith)—important in the benefits section; religiousness or faith.

Intervention:
1. Reconciliation of any potential conflict between needs analysis and stated consumer preferences.
2. Wellness programs.
   a. Weight management (overweight, obese, morbidly obese).
   b. Stress/anger management.
   c. Fitness & hobby.
   d. Smoking cessation.
   e. Nutrition.
   f. Sleep.
   g. Circle of support-group friends.
3. Personal Nurse (PN)/Disease Management (DM) programs: Pregnancy; Diabetes; Heart disease; Cancer; Back pain/arthritis; Rare disease; Osteoporosis; Stroke; Obesity; High blood pressure; Alzheimers; Asthma; Kidney; and Mental health/depression.

Ortho Tailored Content:
1. Personalized letter (INABC—Introduction; Needs analysis; Action plan; Benefits; Closing motivational message).
2. Condition center (for members with at least 1 chronic condition: 37.1% commercial).
   a. Tailored Universal Resource Location (URL) list for helpful health content.
   b. Health tips for self-management of chronic conditions (Kate Lorig).
3. Fun & games.
4. Health scores—Current; Tracking.
5. Behavioral feedback—"Keep doing . . . "; "Please improve . . . ".
6. General health tips and comic strips—How to work out without really trying; and similar.

Figure 1:
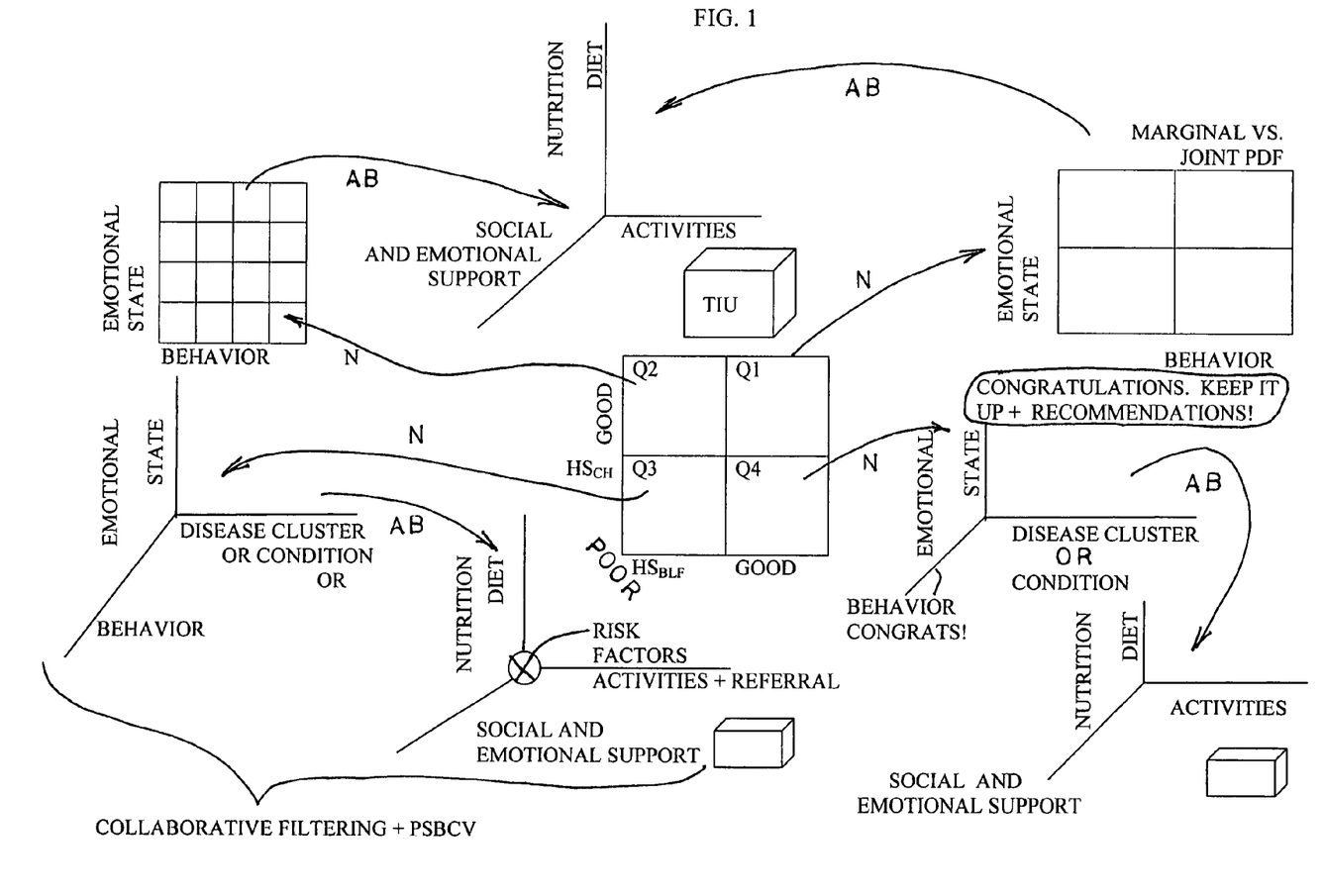

Personalized Letter:
% - - - Logic tree.
$HS_{CH}$ vs. $HS_{BLF}$: 2×2 quadrant view.
Chronic condition: none, one, >1.
BMI: <18.5, 18.5-27.5, 27.5-31, and >31.
Stress: family and work.
Exercise: none-to-little, OK subject to the can't-exercise flag.
Eating habit: bad, good.
Smoking: No, occasional, chain.
% - - - Hierarchical embedded content tree.
1. 1. 2×2 cell of $HS_{CH}$ (y) and $HS_{BLF}$ (x) (for example, see FIG. 1).
   a. Q3: Sick with unhealthy behavior.
   b. Q4: Sick, but healthy behavior.
   c. Q1: Model citizen.
   d. Q2: Healthy, but unhealthy behavior.
2. Disease conditions: Organize information based on hierarchical Major Clinical Condition (MCC).
   a. Amenable to behavioral intervention to improve current conditions and/or retard disease progression (diabetes, heart disease, asthma, some cancer, mental, risk (RSK), musculoskeletal (MUS)).
   b. Conditions that require concentrated intervention and, if successful, major benefits possible: Chronic Obstructive Pulmonary Disease (COPD).
   c. Too late or less amenable to behavioral intervention and requires DM intervention if applicable (HIV, End stage renal disease ESRD/Chronic Kidney Disease CKD, some cancer, rare disease RAR, transplant TRA).
3. Unhealthy behaviors conditioned upon BMI and waist circumference—Smoking; Stress; Exercise; Eating Habits.
4. Lifestyle issues—Loneliness and friends.
5. Constraints & customization.
   a. Stated preferences in wellness and DM programs.
   b. Psychosocial behavioral profiles.
      i. Self-efficacy.
      ii. Motivation.
      iii. Emotional attribute trade off.
% - - - Fran's reduced-order-tree structure for prototype implementation.

Figure 2:
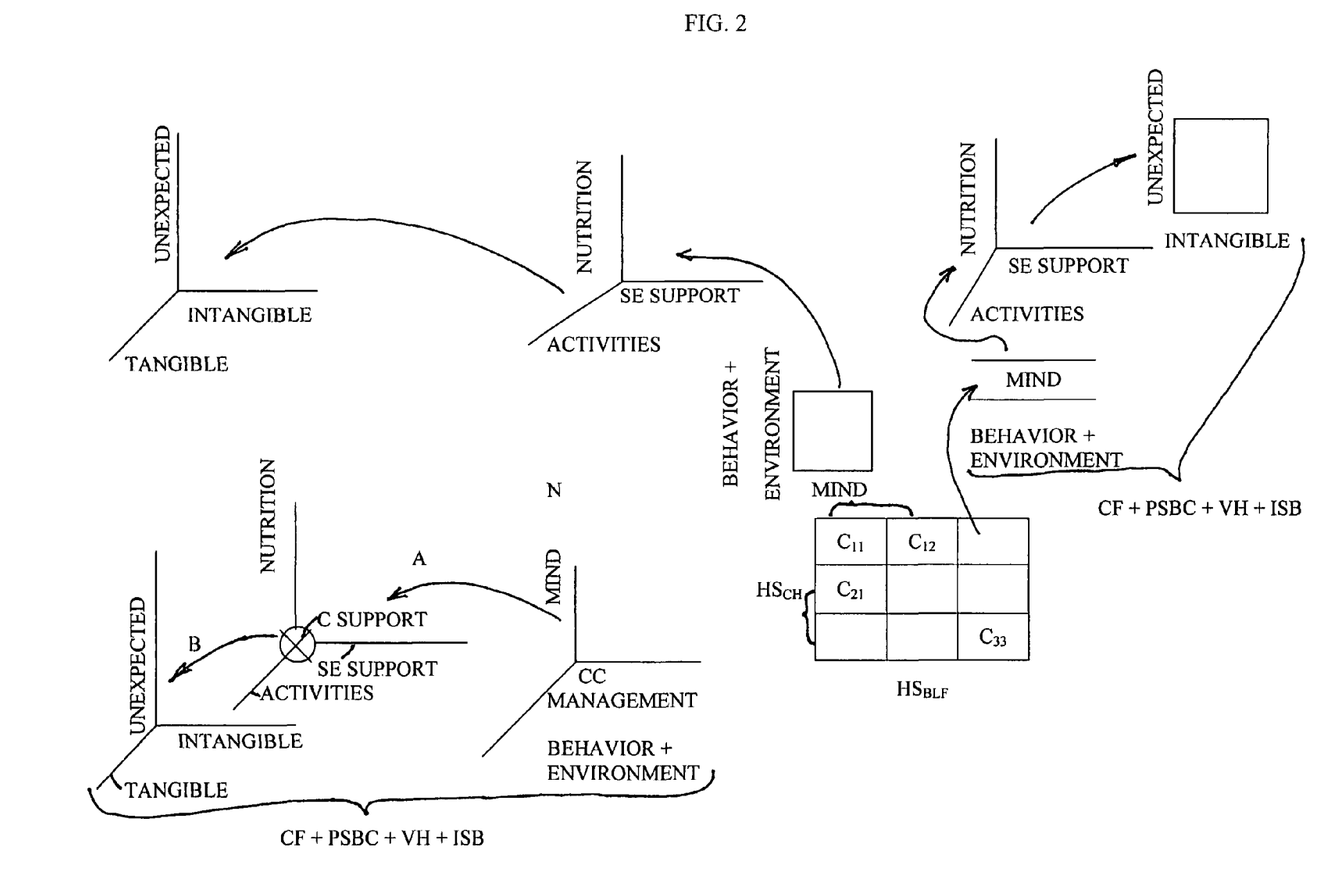

Needs analysis (HSo=health score overall, HSp=health score peer).
1. HS (1=excellent, 2=good, 3=improving, 4=poor).
   a. HSo=1 & HSp=1, 'ExcellentHS'
   b. HSo=1 & HSp>1, 'goodHSo' - - - similarto 'oneHS'
   c. HSo>1 & HSp=1, 'goodHSp'
   d. HSo=2 & HSp=2 & BLF>4.5, 'decentHS'
   e. HSo=2 & HSp=3 & BLF>4.5, 'oneHS'
   f. HSo=2 & (HSp=2|HSp=3) & BLF<=4.5, 'HealthyBadBLF'
   g. (HSo>=3|HSp=3) & BLF>=6.5, 'BadHealthGoodBLF'
   h. (HSo>=3|HSp=3) & BLF<=4.5 & max(clinical score o,p)>avg, 'BadBLF'
   i. (HSo>=3|HSp=3) & BLF<=4.5 & poor clinical score, 'BadHealthBadBLF'
   j. conditions 7 to 9 do not apply, 'PoorHealth'
2. HS and BMI
   a. (HSo=4|HSp=4) & BMI>=25, 'BMIg25HSbelow4', else 'BMIg25HSabove4'
   b. BMI<18, 'BMItooLow'
   c. (BMI>=27 & little exercise), 'BMIg27noExercise'
   d. (BMI<27 & little exercise), 'noExercise'
   e. Smoking lever>thr, 'smoking'
   f. family/job stress, 'hiStress'
   g. job stress & no vacation>thr, 'needVacation'
   h. loneliness, 'loneliness'
   i. alcohol consumption>thr, 'alcoholComsumption'
   j. premature birth, 'PrematureBirth'
   k. Chronic conditions & (HSo>=3|HSp>=3), 'chronicClinicalProgram'
   l. Chronic conditions & (HS else), 'chronic'
   m. WP conditions (smoking, weight, etc.) exist but not interested in WP, 'preference' - - - need to remove clinical program from this content Action Plan:
1. Chronic condtions & (HSo>=3|HSp>=3), 'chronic-ClinicalProgram'
2. Chronic condtions & (HS else), 'chronic'
3. Bad eating habits>thr, 'badEatingHabbits'
4. Yo-yo dieting, 'weightFL'
5. BMI>25 & chronic conditions & interested in WP, 'BMIg25WmCc'
6. BMI>25 & no chronic condition & interested in WP, 'BMIg25WmNoCc'
7. Smoking & interested in WP, 'smokeCessation'
8. Job stress, 'stressReduceAtWork'
9. Family stress, 'stressReduceAtHome'
10. Loneliness, 'loneliness'
11. interested in cardio workout, 'workout'
12. alcohol consumption>thr, 'alcoholConsumption'
% - - - More detailed progressive content for this project (for example, see FIG. 2)
Case $c_{31}$ (Poor Health and Unhealthy Habits)
1. Boat anchor
  a. Hobbies: Literally sprinkled into every paragraph (quip, humor, empathy, connection)
    i. Leisure activities: reading, writing, golf, movies, walking
    ii. Moderate activities: yoga, stretching
  b. Psychosocial Behavioral Clinical (PSBC)
    i. Motivation: high or low (I'm highly motivated to conquer my health issues.)
    ii. Self-efficacy: high or low (I can do whatever I want.)
    iii. Self-actualization
    iv. Social: Family and friends
    v. Information-seeking behavior
    vi. Demographic variables: Ethnicity, education, age, and gender
  c. Information-seeking behavior:
  d. Value hierarchy: Each value-hierarchy attribute has a score associated with each population cluster as seen in the following Table 1.

vii. Stress
    viii. Unsafe sex
  b. Mind
    i. Loneliness
    ii. Love relationship
  c. Chronic condition (CC) management
    i. None
    ii. 1-2
    iii. >2
4. Action plan
  a. Nutrition
  b. Activity
    i. Kate Lorig's book
  c. Social and emotional (SE) support
    i. Feeling proud of one's body
  d. Clinical support
    i. PN, DM, and case management (CM) programs
5. Benefits
  a. Tangible
    i. Financial
    ii. Physical appearance
  b. Intangible
    i. Happiness with being in better health
    ii. Relationship and fun with friends, children, spouse
  c. Unexpected
6. Concluding motivational message
Case $c_{13}$ (Model Citizen)
1. Introduction
2. Needs analysis
  a. Behavior+environment
  b. Mind
3. Action plan
  a. Nutrition
  b. Activity
  c. SE support
4. Benefits
  a. Tangible
  b. Intangible

TABLE 1

| Attribute | Emotional | Practical | Ambitious | Religious |
|---|---|---|---|---|
| Love | 10, 7, 3, 0, −1, −3, −5 | −5, 3, −1, 0, 1, 3, 5 | −3, −2, −1, 0, 0, 0, 0 | 5, 3, 1, 0, −1,−3, −5 |
| Power | −5, −3, −1, 0, 1, 3, 5 | 5, 3, 1, 0, −1, −3, −5 | 10, 7, 3, 0, −1, −3, −5 | −3, −2, −1, 0, 1, 2, 3 |
| Money | −5, −3, −1, 0, 1, 3, 5 | 10, 7, 3, 0, −1, −3, −5 | 5, 3, 1, 0, −1, −3, −5 | −3, −2, −1, 0, 1, 2, 3 |
| Family | 5, 3, 1, 0, −1, −3, −5 | 3, 2, 1, 0, −1, −2, −3 | −3, −2, −1, 0, 1, 2, 3 | 3, 2, 1, 0, −1, −2, −3 |
| Friends | 5, 3, 1, 0, −1, −3, −5 | 3, 2, 1, 0, −1, −2, −3 | −3, −2, −1, 0, 1, 2, 3 | 3, 2, 1, 0, −1, −2, −3 |
| Faith | 3, 2, 1, 0, −1, −2, −3 | 0 | 0 | 10, 7, 3, 0, −1, −3, −5 |
| Health | −3, −2, −1, 0, 1, 2, 3 | 5, 3, 1, 0, −1, −3, −5 | 3, 2, 1, 0, −1, −1, −1 | 0 |

2. Introduction:
3. Needs analysis
  a. Behavior+environment
    i. Smoking
    ii. Drinking and/or substance abuse
    iii. Premature birth
    iv. Abnormal BMI
      1. Yo-yo diet trend
    v. Poor eating habits
    vi. Lack of exercise 5. Concluding motivational message
% - - - Partial content example
Introduction Thank you for participating in this year's challenge. I will do everything possible to help you enjoy a healthier, happier, and fuller life. I sincerely hope that we can have a long-term relationship despite the fact that I exist in cyberspace. My goal is to look after you in every possible way. Please take a deep breath and let me show you the way.

Needs Analysis

In this section, I will provide you with the summary of your unique needs that I identified from your challenge. Furthermore, I will take your preferences and privacy issues into consideration in devising a tailored action plan just for you.

1. Needs analysis
   a. Q3: I'm sorry to be the bearer of bad news, but you have a lot of room for improvement in your health. I hope you don't execute me for bringing the bad news to you as I have nothing but good intentions for you. Please open your mind and accept my constructive tips as it is always better to be late than never.
   b. Q4: It seems that you have some chronic conditions that require self-management and that you've been making a conscientious effort to live a healthier life. I congratulate you on your efforts. I will help you improve your current practices and find new opportunities for improvement so that you will be even healthier and happier.
   c. Q2: It seems that while you are generally healthy, you seem to have acquired some unhealthy habits that may hurt you in the long run. Up to ⅔ of health problems that develop during later stages of one's life can be alleviated through early adoption of healthy lifestyles. Do you remember your financial advisor's recommendation that the earlier you save, the earlier you can retire. The same logic applies to health. Please let me show you how.
   d. Q1: I have to say you are a model citizen when it comes to your health. Congratulation on your success and please spread the word to your neighbors and coworkers. Nevertheless, please let me help you find ways to make your health life even better.
2. Action plan
   a. Q1:
   b. Q2:
   c. Q3:
   d. Q4:
3. Benefits
   a. Q1:
   b. Q2:
   c. Q3:
   d. Q4:
4. Concluding motivational message
   a. Q1:
   b. Q2:
   c. Q3:
   d. Q4:

Prematurely born & no chronic condition: I must congratulate you on living a healthy life. As you may or may not know, premature birth is often associated with adulthood chronic illnesses, such as diabetes and heart disease. The reason, researchers explain in an Economist article, is that given an environment of scarcity, the baby's body devotes most of the available energy to brain development while the rest of the body is somewhat ignored. Given a less number of redundant parts to start with and a steady failure rate over time, you can imagine that the critical juncture may occur earlier in time for those born prematurely. Luckily, the researchers also found an easy solution that I will share with you shortly.

Premature birth with chronic condition:

If HS in Q1: Your overall and peer health scores of 76 and 82, respectively, indicate you are in excellent (relatively good) health. Congratulations on a beautiful job. You've done yourself and those who love you a huge favor. However, don't be cocky yet. I may find an interesting assignment for you later.

Smoking yes: Do you know that most of the gains in life expectancy during the past several decades can be attributed to smoking cessation? Numerous research papers show that scarred lung tissues can regain their vitality in as little as 6 months after you quit smoking.

If BMI>27.5 and little exercise: While there is no immediate concern, given your BMI of 29.3 and reported lack of exercise, you may benefit from being a little more active. Let me show you how you can energize your body and mind without consciously trying.

If one of HS is between 50 and 70:

If 30≤at least one HS<50: While your overall health score of 52 is decent, your peer health score of 39 indicates that there is room for improvement. I hope you will be receptive to my constructive message to help you improve your score. Please remember I'm your personal health Genie in cyberspace.

If both HS<30: Your overall health score (whichever is higher) of 25 indicates that you haven't had a good year in terms of your health. I will help you enjoy life more through a number of concrete and actionable steps. I would greatly appreciate it if you act upon my carefully crafted action plan.

If BMI>25 & HS≥30: Your BMI is 28.3. In a developed world, avoiding sedentary life is one of the biggest challenges. In the U.S. alone, over 55% of adults and 25% of teenagers are overweight or obese. While BMI is not the best indicator of fitness or health, it is important to realize that extra weight can slow everyone down. Just imagine walking with an extra 10-lbs weight attached to your abdomen. On the other hand, how would you feel if you can run around without the extra weight? Your joints will thank you. Just remember Shaq's nagging injuries associated with his extra weight needed to fight all the big men in the NBA's Western conference. Luckily, you don't need to bulk up like him since you don't have to play against Tim Duncan (men interested in basketball). Think of doing something similar based on hobbies indicated in the CF page.

If BMI>25 & HS<30: Have you considered the possibility that your excess weight might be contributing to your chronic conditions? It is imperative that you take this matter seriously.

If stress=high (job or family): When was the last time you were truly happy? Do you find yourself reminiscing often to escape from today's harsh reality? Bobby McFerrin says, "Don't worry . . . Be happy." Is it that simple? Please think for a while. What is important to you? What makes you happy?

Chronic conditions: I'm sorry that you have xyz chronic conditions. However, thanks to modern medicine and abundance of information, we can work together to help you take control of your medical conditions. Please don't worry, be happy.

Little to no exercise: While it is very difficult to find time to exercise regularly with work and family obligations, I still think it is important for you to set aside a few minute to yourself everyday so that you have time to heal and rejuvenate your mind and body. As D. H. Lawrence said once, "life is ours to be spent, not to be saved."

Loneliness (interest in forming support-group friends and few true friends; perhaps being single with no significant other): Do you remember what Mickey said at the end of the movie Hannah and Her Sisters watching the reflection of his pregnant wife Holly in a mirror? I don't remember the exact quote, but it had something to do with the resiliency of human heart. Mickey was devastated when Hannah left him, only to find love in Holly whom he despised in the beginning. Please watch the movie and witness the magic of human heart—so fragile at times, but resilient when it matters. Another movie that deals with the loneliness issue is Wong Kar-Wei's Chungking Express. (If Asian/Pacific islander & enjoys watching movies)

Reconciliation with consumer preference: While you have xyz conditions and may benefit from considering wellness and clinical programs in yzw areas, you expressed little interest in them. If there is one thing I would like to avoid, it is that I never nag you. However, when you change your mind, please come back to me and give me an opportunity to guide you through the travails of your journey.

Action Plan

Given all your needs and stated preferences, here is a succinct summary of your action plan.

Recommended goals:

1. BMI>25 & interest in weight management & chronic condition: Convert 20 lbs of fat into 10 lbs of muscle . . . How? You've got to spend a little money to stay fit. As a minimum, buy dumbbells and strap-on weights for your ankle. In order to accelerate payoff, spend 10-15 minutes everyday walking or jogging with the strap-on weights and 10-15 minutes without it. Next spend 10 minutes lifting dumbbells while you watch your favorite TV show. You can achieve your goal as long as you do it consistently.

2. BMI>25 & interest in weight management & no chronic condition: Convert 25 lbs of fat into 10 lbs of muscle . . .

3. A lot of weight fluctuations: I'm sorry that you've had to endure ups and downs of weight battles. As a wise man in Japan once said, "Every battle is not won by advance. Every retreat is not loss. Advance is strategy. Retreat is also strategy . . . Appearance in retreat is also strategy." What does this gibberish mean? Nobody follows a straight trajectory to the finish line in real life. The more you learn about yourself through your journey, the wiser you become. Don't ever give up.

4. Eating disorder (overeating): Have you heard of French paradox? They eat whatever they want while staying thin and healthy. Some say the magic is in wine. I say the truth is more complex, which may never be known completely. First of all, food is your friend, not enemy. Second, everything in moderation is beneficial. Third, laughter is good anytime. Sounds like a riddle? Think about it for a while and let me know if you get it.

5. Stress reduction at workplace: There is no easy solution especially if you can't stand your boss or coworkers. One option is to transfer to a different department headed by a benevolent Zen Buddhist. If this is not viable, you can always find a new job, hopefully nearby, because relocating to a new job can be very stressful. If none of these are possible, what can you do? I really don't know. I can only say that whatever is holding you back spiritually, please remember you live only once. Youth passes you by in the blink of an eye. Trust me. Time passes by much faster in cyberspace. Try to patch up whatever differences you may have. Have a heart-to-heart talk because life is too short to live like that. Don't you agree? It is incumbent upon you to make your workplace as enjoyable as possible. Please give it a try. I beg you.

6. Stress reduction at home: I think it is presumptuous of me to offer you an advice here. All I can say is that you have to be honest with yourself and your family. It is your life. You deserve to be happy and live a fulfilling life. The same applies to your family members. It is better to give than to take.

7. Working out: Endurance, cardio, and endurance . . . Sweating during workout can improve blood circulation, kill dead skins, and make you look beautiful and glowing afterwards. At the same time, you can socialize with interesting people and make friends. (HS>30, workout with others preferred)

8. Dealing with loneliness: Life is much more than just work. There are numerous opportunities to help and meet interesting people. Just think of all these volunteers to help victims of the horrendous Asian tsunami recently. You just need to look for it and go for it. Sometimes, your heart will be broken, but it is better to have your heart broken and move on than to have your heart never broken at all.

9. Smoking cessation: Just imagine how much Johnny Carson must've suffered for at least a year before his unfortunate passing away on Jan. 23, 2005. Do you know what it's like to suffer from emphysema? You feel like you are drowning with every breath because of the irreversible damage to your lungs. Is smoking really worth it? I suggest you keep smoking if you know you have a smoking-neutralization gene. Otherwise, please quit immediately for you. And for your family members who love you. Science shows that no matter how long you've been smoking, you will be impressed that your body's resilience can perform amazing miracles. Please do, please do. The Beatles sing for you.

10. Dealing with chronic conditions: Good news is that after reaching a peak at the age of 12, everyone goes downhill as you can see here. That is, everyone is in the same boat. Bad news is that chronic conditions, unless properly managed, can lead to accelerated health and functional decline, leading to poorer quality of life. Furthermore, it is only natural for you to feel resentful about your conditions. For more detailed information on how to manage your conditions, I provide comprehensive Web resources as part of tailored feedback. Here, I would like to remind you of three simple things. First of all, it is never too late to start something that's meaningful to you and your family, such as improving your health and happiness. Second, you must want to succeed. The mind-body connection has been clearly established. Third, nothing is impossible. You can do anything if you put your mind into it.

Benefits

Just imagine having more energy to play with your kids (grandkids). Just picture yourself in a swimming suit sunbathing in the Bahamas watching sunset, mesmerized by all the mesmerizing stares from onlookers. Suddenly your love life picks up steam and you find yourself singing in the rain just like Gene Kelly. Why? Because you trusted me! Let me state without ambiguity potential benefits you will enjoy if you follow my action plan designed for you.

High BMI and information-seeking behavior: According to an article by Harvard researchers published in the New England Journal of Medicine, there is a direct relationship between obesity+inactivity and morbidity/mortality. They followed 116,564 women for 24 years and found that the risk factors in comparison to lean, active women (BMI<25 and at least 3.5 hours of exercise per week) were 1.5, 1.91, and 2.42 for lean/inactive women, obese/active women, and obese/inactive women, respectively. I know it is dry science, but if you do nothing to change your future, you are 2.42 times more likely to suffer from chronic illnesses than what you can become if you let yourself explore the unknown with me.

1. Overweight/obese: Just take a look at these people here: http://www.healthyweightforum.org/eng/forum/forum_topics.asp?FID=50. It is a support-group Web site dedicated to people who want to lose weight and stay healthy. While many focus on looks, there are many more important health benefits: http://www.lifeclinic.com/focus/nutrition/losing-weight.asp.

2. Chronic conditions: Provide URLs from Healthwise and other Web sites.—Pregnancy; Diabetes; Heart disease; Cancer; Back pain/arthritis; Rare disease; Osteoporosis; Stroke; Obesity; High blood pressure; Alzheimers; Asthma; Kidney; Mental health/depression.

3. Stress:

4. Nutrition:

Concluding Motivational Message

I can't thank you enough for getting this far with me. When was the last time you felt that you could move the earth? Do you feel the same way now? If yes, excellent! Just go for it. In Million Dollar Baby, an unusual combination of two people creates magic through their desire, hard work, and perseverance. You are worth it and you can improve your life only if you want it. Please want it. Bad enough! Bless your heart for wanting it!

Health and Life Tips:

Tips for working out without consciously trying:

1. If possible at work, try stairs instead of elevators. Stair-climb workout is "one of the most efficient ways to work all the muscles in your thighs, hips, and buttocks, while remaining injury-free." Source: RunnersWorld, February 2005.

2. Park far away from mall entrances during daytime (night time if you have a third-degree black belt in TaeKwonDo). As a bonus, your car will thank you for no more facial blemishes.

3. While watching NFL or NBA games, do sit-ups or lift dumbbells. Every time your team or your favorite NBA player (hopefully NBA's top scorer) scores, jump up and down for 15 seconds with your hands clapping.

4. Always carry a pair of walking shoes in your car. That way, after eating a big meal at Martini's, you can always walk around the Summit a few times while having a mind-bending conversation with someone you love.

5. Annoy your boss and take a 5-minute walk at least twice a day, if possible with your favorite coworker. Even better, take the stairs together. This might be one way to blossom your office romance in secret (R rated).

6. Exercise your brain. How? Think!

7. Escape from your daily grind and find exotic, romantic places so that you can have some fun with your spouse.

Tips for healthy eating and cooking:

1. When eating out, share a meal since there is plenty for both of you. If this is embarrassing, order the second dish for a takeout.

2. Drink water instead of carbonated drinks. If you must, drink diet soda.

3. Avoid all-you-can-eat buffets unless you intend to hibernate like a cuddly bear.

4. If possible, start each meal with salad with dressing on the side.

5. Give your body credit. Eat when you are hungry. Also stop when you are no longer hungry.

6. Drink a lot of water. Remember every time you get up to go to the washroom, you have water cleansing your body as well as walking. Ask your boss to assign you to an office farthest from the washroom.

7. Avoid hydrogenated fats and oils. Remember how your hand feels after you change engine oil. Just imagine your heart blood vessels coated in sticky oil.

8. Don't overcook vegetables.

9. Have fun while eating. Eat slowly while savoring every obscure flavor hidden in your food. Let your tongue be the greatest food detective as well as a talking agent.

Tips for walking:

1. Bend your elbows. Why? Think about the torque theory that you learned in high school physics.

2. Think heal-to-toe.

3. Keep your abs pulled in and tight. Think of Billy Blanks in his Taebo DVD. Always tighten your stomach muscle while walking.

4. Monotony is boring. See if you can walk fast for a short period of time as long as it doesn't crimp your style.

5. Keep Nike, Puma, Reebok, and Adidas happy. Replace your shoes after 250-500 miles of walking. For most people, that's every 1-2 years.

Low BMI, bad eating habit:

Your eating habit is not very good, but you have a slender figure, that means you are under eating or you were born with it. Lots of people probably admire you for having a slim figure is highly desirable nowadays. However, you need good nutrition for your body to function, just like you need the right fuel for your car to run. Malnutrition leads to various health problems due to protein, calorie, vitamin, or mineral deficiencies.

Taste a rainbow of fruits and vegetables for better health. Think colors—blue/purple, green, white, yellow/orange, and red. Eat moderately, regularly and slowly. Never over eat or under eat. Eat lean meats and other good sources of protein, such as eggs and nuts. Choose whole-grain breads and cereals. Limit fast food and other low-nutrient snacks. Limit intake or fat and sugar. Do not use eating as an emotional rescue.

High HS:

Congratulations! You have been taking good care of yourself both physically and mentally. If more people in this country are like you, we will be healthier, happier and more productive. Now comes the questions—how to keep up with the good work?

HS 30-50, chronic condition 1:

Half Empty or Half Full?

Your health may not be in perfect condition and your chronic condition may have been causing you inconveniences in daily life. However, there are always two sides of a situation. Will you say a half glass of water is half-empty or half-full?

Instead of pitying yourself of having a chronic condition, you may realize that you have been taking so many simple things and pleasurable moments in life for granted, like your health, friends' or family's love or your ability to work . . .

Your choice is to focus on the positive now. Ask yourself that—What have I lost and what have I gained? It can be an opportunity to learn more about your inner strength and the importance of the people in your lives. You may have already found that so many people are concerned about you. It is also a chance to develop your gifts that have lain dormant within and to care for yourself in new and profound ways.

Smoking: Is it worth it? You must have learned about the cons of smoking and second-hand smoking—cancer, bronchitis, COPD, yellow skin and teeth, smelly clothes, constant and nagging cough, holes burnt in your furniture and clothes, going out in late night/bad weather to smoke and to buy cigarettes, guilt, feeling discriminated in non-smoking areas . . . You probably know very well how to finish this list. So what are the pros? Cool image? Bonding with other smokers? Momentary gratification? I guess those are pretty much all. I let you decide if they are worthy of sacrificing your health.

Stress: Laugh it away . . . When you are under stress, your muscles become tense, your heart beats faster, blood pressure goes higher, you sweat and feel fatigue. You are more likely to feel anxious and withdraw from social interaction. You see how stress can affect you physically, emotionally and socially, so let's LAUGH it away. It is not a joke. Here are some of the findings about humor and laughter:

PSYCHOLOGICAL: Acts as a major coping mechanism; relieves anxiety and tension, serves as outlet for hostility and anger, provides healthy escape from reality, and lightens heaviness related to critical illness, trauma, disfigurement, and death.

SOCIAL: Lessens the hierarchy between individuals, establishes rapport, and decreases social distance.

PHYSIOLOGICAL: Increases respiratory and oxygen exchange, stimulates heart rate and blood pressure followed by a relaxation phase, stimulates muscles and relaxes muscle tension. Tears from a belly laugh provide exocrine response, carrying away toxins found in cells under stress.

Here are a few more tips which I think are useful to handle stress. Try your best but not try to be perfect all the time, forgive others and yourself more often, learn lessons from failures and then let go, exercise regularly, develop hobbies, simplify your life, don't drown yourself in chores—think BIG.

The foregoing disclosure enables one skilled in the art to practice the following method and to construct a system for its implementation: A method for providing individually tailored healthy behavior-promoting information to an individual, the method comprising the steps of: mapping the health status of the individual on the basis of information available concerning the individual with respect to the individual's clinical and disease history and the individual's behavioral and lifestyle and family history, thereby creating a multidimensional map position concerning the individual; eliciting from the individual one or more answers to questions concerning the individual's preferences and tendencies, thereby creating an answer set concerning the individual; and providing to the individual, in a format that varies according to the answer set, one or more recommendations concerning one or more behaviors in which the individual can engage in order to maintain or improve the individual's health, wherein the one or more recommendations comprise content that varies according to the map position and the answer set.

The foregoing detailed description is given primarily for clearness of understanding and no unnecessary limitations are to be understood therefrom for modifications can be made by those skilled in the art upon reading this disclosure and may be made without departing from the spirit of the invention and scope of the appended claims.

What is claimed is:

1. A system for providing individually tailored health promoting information, comprising:
   a server system including:
   a response database containing individual responses to health risk assessment questions, behavior questions, lifestyle questions, and family history questions;
   a content database;
   a claims database; and
   a processor; said server system creating a single multidimensional map position for an individual from information on said individual contained in said response database and said claims database, and said server system providing tailored content for said individual from said content database, said tailored content selected based on said individual's multidimensional map position and based on information on that individual contained in the response database and the claims database concerning that individual's self-efficacy, motivation, value hierarchy, faith, and preferred level of content spice;
   wherein selecting said tailored content comprises:
   a) selecting first level tailored content;
   b) selecting second level tailored content; and
   c) selecting third level tailored content;
   wherein said selecting first level tailored content comprises:
   calculating a clinical and disease history health score for said individual;
   calculating a behavioral, lifestyle, and family history health score for said individual;
   designating each of said clinical and disease history health score and behavioral, lifestyle, and family history health score as one of good and poor;
   categorizing said individual in one of four categories based on said individual's health scores: (1) good clinical and disease history and good behavioral and lifestyle and family history, (2) good clinical and disease history and poor behavioral and lifestyle and family history, (3) poor clinical and disease history and poor behavioral and lifestyle and family history, and (4) poor clinical and disease history and good behavioral and lifestyle and family history; and
   selecting content from said content database tailored to said individual's category.

2. The system of claim 1, further comprising at least one user computer which provides said individual access to said server system to receive that individual's tailored content.

3. The system of claim 2, where said at least one user computer permits said individual to provide information for said response database related to that individual.

4. The system of claim 1, where said individual's multidimensional map position is based on available information on that individual contained in the response database and the claims database concerning that individual's clinical and disease history and that individual's behavioral and lifestyle and family history.

5. The system of claim 4, where said individual's tailored content is based on available information on that individual contained in the response database and the claims database concerning that individual's weight, eating habits, exercise habits, family support structure, stress management, hobbies/activities, smoking/non-smoking, sleep habits, disease conditions, emotional issues, age, and gender.

6. The system of claim 1, where said value hierarchy includes the attributes love, power, money, family, friends, faith, and health.

7. The system of claim 1, wherein said tailored content includes advising said individual that improving said individual's health status results in increased chances for romance.

8. The system of claim 1, wherein selecting first level tailored content comprises selecting content from said content database tailored to said individual's reported behavior regarding at least one of: eating, stress, weight, fitness, sleep, and smoking.

9. The system of claim 1, wherein content within said content database is associated with at least one of a plurality of value hierarchy attributes, each value hierarchy attribute having a score associated with each of a plurality of population clusters, and wherein selecting first level tailored content comprises:
   assigning said individual to one of said plurality of population clusters; and
   selecting content from said content database associated with the value hierarchy attributes preferred by said individual's population cluster.

10. The system of claim 1, wherein selecting second level tailored content comprises selecting content that includes an analogy comparing said individual's health status to that of one of: a professional athlete and a celebrity.

11. The system of claim 1, wherein selecting second level tailored content comprises selecting content that includes a reference to one of: a movie relevant to said individual's health status and a book relevant to said individual's health status.

12. The system of claim 1, wherein selecting third level tailored content comprises selecting content that informs said individual of personal services relevant to said individual's health status, said personal services including at least one of: personal trainer services, personal nutritionist services, and personal nurse services.

* * * * *